(12) United States Patent
Joo et al.

(10) Patent No.: US 12,017,974 B2
(45) Date of Patent: Jun. 25, 2024

(54) ADAMANTANECARBOXYLIC ACID BENZYL AMIDE DERIVATIVE COMPOUND AND SKIN WHITENING COMPOSITION COMPRISING SAME

(71) Applicant: AMOREPACIFIC CORPORATION, Seoul (KR)

(72) Inventors: Yunghyup Joo, Yongin-si (KR); Jaeyoung Ko, Yongin-si (KR); Jaewon You, Yongin-si (KR); Yong Jin Kim, Yongin-si (KR); Tae Ryong Lee, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 436 days.

(21) Appl. No.: 17/418,940

(22) PCT Filed: Jan. 3, 2020

(86) PCT No.: PCT/KR2020/000112
§ 371 (c)(1),
(2) Date: Jun. 28, 2021

(87) PCT Pub. No.: WO2020/141927
PCT Pub. Date: Jul. 9, 2020

(65) Prior Publication Data
US 2022/0112156 A1    Apr. 14, 2022

(30) Foreign Application Priority Data
Jan. 4, 2019 (KR) .................. 10-2019-0001059

(51) Int. Cl.
| C07C 233/60 | (2006.01) |
| A61K 8/42 | (2006.01) |
| A61K 9/00 | (2006.01) |
| A61Q 19/02 | (2006.01) |
| C07C 231/02 | (2006.01) |

(52) U.S. Cl.
CPC .............. *C07C 233/60* (2013.01); *A61K 8/42* (2013.01); *A61K 9/0014* (2013.01); *A61Q 19/02* (2013.01); *C07C 231/02* (2013.01); *A61K 2800/43* (2013.01)

(58) Field of Classification Search
CPC ...... C07C 233/60; C07C 231/02; A61Q 19/02
See application file for complete search history.

(56) References Cited

U.S. PATENT DOCUMENTS

| 4,053,509 A * | 10/1977 | Faro ................ C07D 317/58 |
| | | 564/219 |
| 8,063,248 B2 | 11/2011 | Smith et al. |
| 9,254,251 B2 | 2/2016 | Joo et al. |
| 10,385,011 B2 | 8/2019 | Joo et al. |

FOREIGN PATENT DOCUMENTS

| EP | 1402887 A1 * | 3/2004 | ............. A61K 31/17 |
| KR | 10-2008-0027352 A | 3/2008 | |
| KR | 10-2013-0015954 A | 2/2013 | |
| KR | 10-2013-0107616 A | 10/2013 | |
| KR | 1020130107616 | * 10/2013 | |
| KR | 10-2016-0116861 A | 10/2016 | |
| WO | 2006/138660 A2 | 12/2006 | |

OTHER PUBLICATIONS

Machine translation of KR10-2013-0107616. Accessed Nov. 2, 2023, pp. 1-7 (Year: 2023).*
Cho, Jun-Cheol, et al., "The Depigmenting Activities of Hydroxyl Carboxamide Derivatives Containing Hydrophobic Moiety", Bull. Korean Chem. Soc., 2012, vol. 33, pp. 1333-1336.
International Search Report issued in PCT/KR2020/000112 dated Apr. 13, 2020, 2 pages.
CAS:1774983-96-8, STN Registry Database, (Jun. 7, 2015), 1 page.
CAS:1178763-65-9, STN Registry Database, (Sep. 1, 2009), 1 page.

* cited by examiner

*Primary Examiner* — Andrew S Rosenthal
(74) *Attorney, Agent, or Firm* — Rothwell, Figg, Ernst & Manbeck, P.C.

(57) ABSTRACT

The present specification relates to an adamantanecarboxylic acid benzyl amide derivative compound, an isomer thereof, a pharmaceutically acceptable salt thereof, a hydrate thereof or a solvate thereof, and a skin whitening composition comprising the same as an active ingredient. Specifically, the compound, according to the present specification, is a compound having a novel structure having adamantanecarboxylic acid bound to an amine compound, and exhibits a skin whitening effect by inhibiting the production of melanin, and thus may be used in various ways as a pharmaceutical composition, a cosmetic composition or a skin preparation for external use.

9 Claims, No Drawings

ADAMANTANECARBOXYLIC ACID BENZYL AMIDE DERIVATIVE COMPOUND AND SKIN WHITENING COMPOSITION COMPRISING SAME

CROSS-REFERENCE TO RELATED APPLICATIONS

The present application is a 371 national phase entry of PCT/KR2020/000112, which was filed on Jan. 3, 2020 and designates the United States, which claims priority to Korean Patent Application No. 10-2019-0001059 filed on Jan. 4, 2019 in the Republic of Korea, the disclosures of which are incorporated herein by reference in their entireties.

TECHNICAL FIELD

The present disclosure relates to an adamantanecarboxylic acid benzyl amide derivative compound, an isomer thereof, a pharmaceutically acceptable salt thereof, a hydrate thereof or a solvate thereof, and a skin whitening composition including the same as an active ingredient.

BACKGROUND OF THE INVENTION

The skin has physical and chemical UV protecting factors and has a function for preventing skin disorders caused by various photochemical reactions significantly. A horny layer reflects and diffuses ultraviolet rays to reduce the energy thereof. In addition, melanin pigment, superoxide dismutase (SOD) and the other antioxidant ingredients absorb ultraviolet rays infiltrated into the skin and reduce the energy thereof or scavenge active oxygen generated secondarily by ultraviolet rays, and thus prevent skin disorders.

However, when a large amount of UV rays exceeding the abilities of such protecting factors is irradiated to the living body, or when the abilities thereof are degraded as one grows older, various types of skin disorders occur.

There are many types of cells, such as Langerhans cells, participating in immunity of the living body, in the skin. UV irradiation causes not only numeral reduction of such cells but also functional disorder thereof. The most significant factor of the skin color-determining factors is the distribution state and amount of melanin in the skin. Melanin is produced in melanocytes, and enzymes, such as tyrosinase, are present in melanocytes. In addition, the enzymes and melanocytes function together to cause oxidative polymerization using an amino acid, called tyrosine, present in the living body at all times as a substrate, thereby forming a dark brown pigment, melanin. The formed melanin moves toward the epidermal cells, called keratinocytes, through the dendritic protrusions of melanocytes. Herein, melanin plays importable roles, and for example, it forms a hat-like structure around the nucleus to protect genes from UV rays and scavenges free radicals to protect intracellular proteins.

There is no enzyme decomposing melanin in the living body, and melanin is removed merely by being detached from the skin together with keratinocytes, when keratinocytes are detached from the epidermis. However, when melanin is formed in an undesirably excessive amount, it causes hyperpigmentation, such as freckles and spots, which is a cosmetically undesirable result.

There are several factors known to affect melanin formation. In the cosmetic field, acceleration of melanin formation caused by UV rays and pigmentation caused thereby are important. The fundamental mechanism of a pharmaceutical agent incorporated to a whitening cosmetic product in order to prevent pigmentation is inhibition of the action of tyrosinase, inhibition of tyrosinase formation, inhibition of a melanin-forming mediator, inhibition of reduction and photo-oxidation of the existing melanin, acceleration of melanin discharge, UV cutting, or the like.

Since women have a desire to have white skin even in UV-exposed environments, a need for preventing and alleviating abnormal skin pigment conditions and hyperpigmentation has been increased more and more. Therefore, there has been a need for developing a whitening product capable of preventing excessive melanin formation, and many attempts have been made in this context. Particular examples of such attempts include inhibitors, such as kojic acid or arbutin, for suppressing tyrosinase activity, hydroquinone, vitamin A, vitamin C and derivatives thereof. However, use of the above-mentioned compounds is limited due to the problems related with safety to the skin, stability in a formulation and an insufficient whitening effect.

Meanwhile, as important factors affecting the expression of whitening activity of polyphenol compounds, which have been studied as whitening agents for several years, in terms of the molecular structure, there have been considered the position and number of hydroxyl groups important in terms of hydrogen bonding, intervals between main functional groups bound to receptors, oil solubility suitable for permeation through the cellular membrane, or the like.

Particularly, an adamantane group used as a substituent is added for the purpose of increasing the oil solubility of a compound and absorption thereof. When an adamantane group is added to the existing substances, the oil solubility may be increased excessively to cause a problem related with a formulation. Under these circumstances, there is a need for developing a novel compound which inhibits melanin formation, shows an excellent skin whitening effect, and is free from a formulation-related problem caused by excessive oil solubility.

SUMMARY OF THE INVENTION

A technical problem to be solved by the present disclosure is to provide a novel adamantane carboxylic acid benzyl amide derivative compound which inhibits melanin formation and has an excellent skin whitening effect, and a skin whitening composition including the same.

In one general aspect, there is provided a novel adamantanecarboxylic acid benzyl amide derivative compound, an isomer thereof, a pharmaceutically acceptable salt thereof, a hydrate thereof or a solvate thereof.

In another general aspect, there is provided a method for preparing a novel adamantanecarboxylic acid benzyl amide derivative compound, an isomer thereof, a pharmaceutically acceptable salt thereof, a hydrate thereof or a solvate thereof.

In still another general aspect, there is provided a skin whitening composition including a novel adamantanecarboxylic acid benzyl amide derivative compound, an isomer thereof, a pharmaceutically acceptable salt thereof, a hydrate thereof or a solvate thereof, as an active ingredient.

In one aspect, the novel adamantanecarboxylic acid benzyl amide derivative compound according to the present disclosure inhibits melanin formation and has a whitening effect, and thus can be used widely for a pharmaceutical composition, a cosmetic composition or a preparation for external use on skin.

In another aspect, the novel adamantanecarboxylic acid benzyl amide derivative compound according to the present disclosure is synthesized with an adamantly group not as a substituent but as a main structural part, and thus can solve the formulation-related problem caused by an excessive increase in oil solubility.

Throughout the specification, the expression "a part includes or comprises an element" does not preclude the presence of any additional elements but means that the part may further include the other elements, unless otherwise stated.

DETAILED DESCRIPTION

Hereinafter, the present disclosure will be described in more detail.

In one aspect of the present disclosure, there is provided an adamantanecarboxylic acid benzyl amide derivative compound represented by the following Chemical Formula 1, an isomer thereof, a pharmaceutically acceptable salt thereof, a hydrate thereof or a solvate thereof:

[Chemical Formula 1]

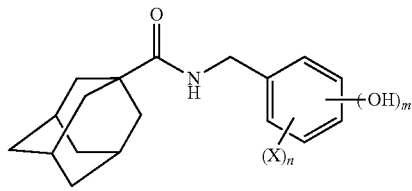

wherein m is an integer of 1-4,

X represents a C1-C6 alkyl group or a C1-C6 alkoxy group, and

N is an integer of 0-3.

The compound according to the present disclosure is synthesized with an adamantly group not as a substituent but as a main structural part so that it may have suitably controlled oil solubility. Therefore, the present inventors have derived a novel type of compound having an excellent whitening effect without excessive oil solubility through the amide bonding of an amine compound having a known phenol structure.

According to an embodiment, m may be an integer of 1-4, preferably 1 or 2.

Herein, the alkyl group may be a linear or branched alkyl group and may not be particularly limited in the number of carbon atoms. Particular examples of the alkyl group include methyl, ethyl, propyl, or the like, but are not limited thereto.

Herein, the alkoxy group may be a linear or branched alkoxy group and may not be particularly limited in the number of carbon atoms. Particular examples of the alkoxy group include methoxy, ethoxy, n-propoxy, isopropoxy, or the like, but are not limited thereto.

According to an embodiment, n may be an integer of 0-3, preferably 0 or 1.

As used herein, the term "isomer" includes not only optical isomers (e.g. essentially pure enantiomers, essentially pure diastereomers or a mixture thereof) but also conformational isomers (i.e. isomers merely having a different angle in at least one chemical bonding), positional isomers (particularly, tautomers), or geometric isomers (e.g. cis-trans isomers).

As used herein, the term "essentially pure" used with reference to enantiomers or diastereomers means that a specific compound exemplified by an enantiomer or diastereomer exists at about 90% or more, preferably about 95% or more, more preferably about 97% or more, or about 98% or more, even more preferably about 99% or more, and most preferably about 99.5% or more (w/w).

As used herein, the term "pharmaceutically acceptable" means that use of a compound in a general medicinal dosage avoids a significant toxic effect, and thus the compound can be approved by the government or other regulatory organizations corresponding thereto for animal use, or particularly for human use, or the compound is listed in a pharmacopoeia or is regarded as a general pharmacopoeia.

As used herein, the term "pharmaceutical acceptable salt" means a salt according to an embodiment of the present disclosure, which is pharmaceutically acceptable and has preferred pharmacological activities of its parent compound. The salt may include: (1) an acid addition salt formed with an inorganic acid, such as hydrochloric acid, hydrobromic acid, sulfuric acid, nitric acid or phosphoric acid, or formed with an organic acid, such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, bezoic acid, 3-(4-hydroxybenzoyl)bezoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tert-butyl acetic acid, laurylsulfuric acid, gluconic acid, glutamic acid, hydroxynaphthoic acid, salicylic acid, stearic acid or muconic acid; or (2) a salt formed upon the substitution of an acidic proton present in its parent compound.

As used herein, the term "hydrate" is a compound to which water is bound, and is used as a broad concept covering an inclusion compound having no chemical binding force between water and a compound.

As used herein, the term "solvate" means a high-order compound formed between a solute molecule or ion and a solvent molecule or ion.

According to an embodiment, the compound represented by the above Chemical Formula 1 may be represented by any one of the following Chemical Formula 1-1 to Chemical Formula 1-7:

[Chemical Formula 1-1]

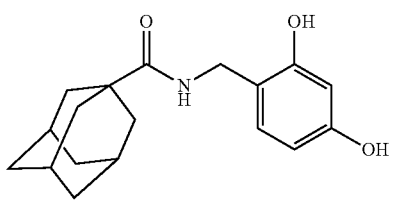

[Chemical Formula 1-2]

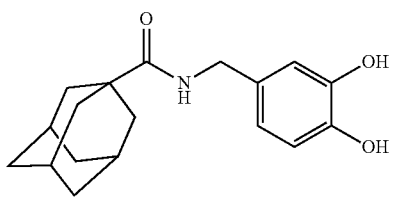

-continued

[Chemical Formula 1-3]
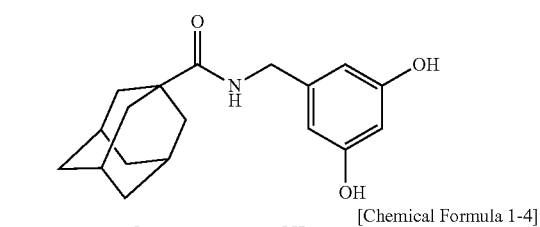

[Chemical Formula 1-4]
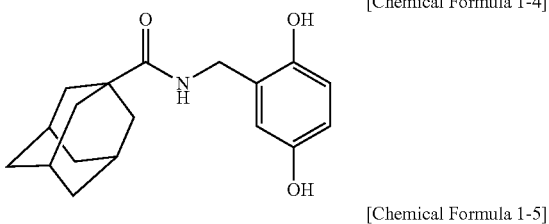

[Chemical Formula 1-5]
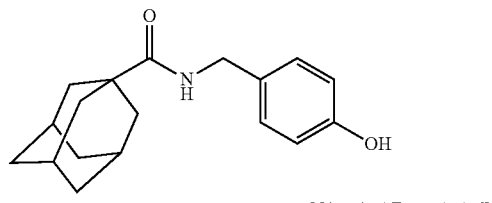

[Chemical Formula 1-6]
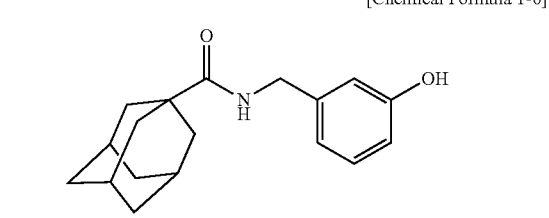

[Chemical Formula 1-7]
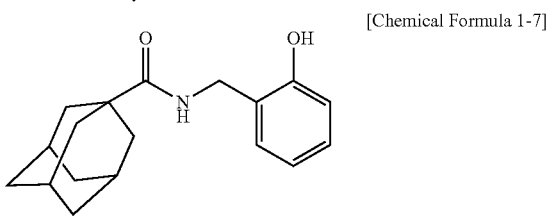

The IUPAC name of the adamantanecarboxylic acid benzyl amide derivative compound represented by Chemical Formula 1-1 is adamantane-1-carboxylic acid 2,4-dihydroxy-benzylamide.

The IUPAC name of the adamantanecarboxylic acid benzyl amide derivative compound represented by Chemical Formula 1-2 is adamantane-1-carboxylic acid 3,4-dihydroxy-benzylamide.

The IUPAC name of the adamantanecarboxylic acid benzyl amide derivative compound represented by Chemical Formula 1-3 is adamantane-1-carboxylic acid 3,5-dihydroxy-benzylamide.

The IUPAC name of the adamantanecarboxylic acid benzyl amide derivative compound represented by Chemical Formula 1-4 is adamantane-1-carboxylic acid 2,5-dihydroxy-benzylamide.

The IUPAC name of the adamantanecarboxylic acid benzyl amide derivative compound represented by Chemical Formula 1-5 is adamantane-1-carboxylic acid 4-hydroxy-benzylamide.

The IUPAC name of the adamantanecarboxylic acid benzyl amide derivative compound represented by Chemical Formula 1-6 is adamantane-1-carboxylic acid 3-hydroxy-benzylamide.

The IUPAC name of the adamantanecarboxylic acid benzyl amide derivative compound represented by Chemical Formula 1-7 is adamantane-1-carboxylic acid 2-hydroxy-benzylamide.

In another aspect of the present disclosure, there is provided a method for preparing the above-mentioned adamantanecarboxylic acid benzyl amide derivative compound, including a step of reacting adamantane-1-carboxylic acid with a hydroxybenzylamine derivative.

According to an embodiment, the hydroxybenzylamine derivative may be any one selected from the group consisting of 2,4-dihydroxybenzylamine, 3,4-dihydroxybenzyamine, 3,5-dihydroxybenzylamine, 2,5-dihydroxybenzyl amine, 4-hydroxybenzylamine, 3-hydroxybenzylamine and 2-hydroxy benzylamine.

Particularly, adamantane-1-carboxylic acid is dissolved in dichloromethane and is allowed to react with a hydroxybenzylamine derivative at room temperature in the presence of N-(3-dimethylaminopropyl)-N-ethylcarbodiimide hydrochloride (EDC) and triethylamine. In addition, after completing the reaction, the resultant product is washed, dried, filtered and isolated to obtain a compound represented by Chemical Formula 1, finally.

In still another aspect of the present disclosure, there is provided a skin whitening composition including an adamantanecarboxylic acid benzyl amide derivative compound represented by Chemical Formula 1, an isomer thereof, a pharmaceutically acceptable salt thereof, a hydrate thereof or a solvate thereof, as an active ingredient.

According to an embodiment, the skin whitening composition may include the compound, isomer thereof, pharmaceutically acceptable salt thereof, prodrug thereof, hydrate thereof or solvate thereof, as an active ingredient, in an amount of 0.01-20 wt %, particularly 0.1-10 wt %, and more particularly 0.5-5 wt %, based on the total weight of the composition.

Within the above-defined range, the skin whitening composition is suitable for providing the desired effects of the present disclosure, can satisfy both the stability and safety of the composition, and shows suitable cost-efficiency. Particularly, when the compound, isomer thereof, pharmaceutically acceptable salt thereof, prodrug thereof, hydrate thereof or solvate thereof is used in an amount of less than 0.01 wt %, it is not possible to obtain a sufficient skin whitening effect. When the compound, isomer thereof, pharmaceutically acceptable salt thereof, prodrug thereof, hydrate thereof or solvate thereof is used in an amount of larger than 20 wt %, the cost-efficiency is low undesirably.

According to an embodiment, the skin whitening composition may be applied to various industrial fields, and for example, may be used for a pharmaceutical composition, a cosmetic composition or a preparation for external use on skin. Preferably, it may be used as an active ingredient of a cosmetic composition. Particularly, when the composition includes the adamantanecarboxylic acid benzyl amide derivative compound as an active ingredient, it is possible to inhibit melanin formation, and thus to provide a skin whitening effect.

The skin whitening composition according to an embodiment of the present disclosure may be a pharmaceutical composition, may further include pharmaceutical adjuvants, such as a preservative, a stabilizer, a hydrating agent or an emulsification accelerator, a salt for controlling osmotic pressure and/or a buffering agent, and other therapeutically useful substances, and may be formulated into various preparations for oral administration or parenteral administration.

Particular examples of the preparation for oral administration include tablets, pills, hard and soft capsules, liquid, suspension, emulsion, syrup, powder, micropowder, microparticles, granules, pellets, or the like. Such formulations may include a surfactant, a diluent (e.g. lactose, dextrose, sucrose, mannitol, sorbitol, cellulose and glycine), a lubricant (e.g. silica, talc, stearic acid and magnesium or calcium salts thereof, and polyethylene glycol), or the like, in addition to the active ingredient. In addition, tablets may include a binding agent, such as magnesium aluminum silicate, starch paste, gelatin, tragacanth, methyl cellulose, sodium carboxymethyl cellulose or polyvinyl pyrrolidone. If necessary, tablets may include a pharmaceutical additive, including a disintegrating agent, such as starch, agar, alginic acid or sodium salt thereof, an absorbing agent, a coloring agent, a flavoring agent, a sweetening agent, or the like. Such tablets may be prepared by conventional mixing, granulation or coating processes. In addition, the preparation for parenteral administration may be provided as a formulation for transdermal administration, and particular examples thereof include an injection, a drop, an ointment, a lotion, a gel, a cream, a spray, a suspension, an emulsion, a suppository, a patch, or the like, but are not limited thereto.

The pharmaceutical composition according to an embodiment of the present disclosure may be administered through a parenteral, rectal, local, transdermal or subcutaneous route, or the like.

The effective administration dose of the active ingredient may be determined with ease by those skilled in the art, and the daily dose thereof may be varied with various factors, such as the severity of a disease, time of onset, age, physical state, and complications of a subject to be administered. For example, the pharmaceutical composition may be administered in a daily dose of 1 µg/kg to 100 mg/kg, such as 0.1-20 mg/kg, 0.5-20 mg/kg, or 1-20 mg/kg, and preferably 5-10 mg/kg, once a day to three times (divided dose) per day, but the scope of the present disclosure is not limited thereto.

The skin whitening composition according to an embodiment may be a cosmetic composition, and the appearance of the cosmetic composition may include a cosmetically or dermatologically acceptable medium or base. The formulation may include any formulation suitable for local application. For example, the composition may be provided in the form of a solution, a gel, a solid, a dry slurry product, an emulsion prepared by dispersing an oil phase in an aqueous phase, a suspension, a microemulsion, a microcapsule, a microgranule or an ionic (liposome) and non-ionic sachet dispersant, or provided in the form of a cream, a skin, a lotion, a powder, an ointment, a spray or a conceal stick. Such formulations may be obtained by the methods generally known to those skilled in the art. In addition, the cosmetic composition may be used in the form of a foam or an aerosol composition further including a compressed propellant.

The cosmetic composition according to an embodiment of the present disclosure is not limited to any particular formulation. For example, the cosmetic composition may be formulated into cosmetic products, such as a skin softener, a skin astringent, a skin nutrient, a nutrient cream, a massage cream, an essence, an eye cream, an eye essence, a cleansing cream, a cleansing foam, a cleansing water, a pack, a powder, a body lotion, a body cream, a body oil and a body essence.

When the formulation is a paste, a cream or a gel, carrier ingredients that may be used include an animal fiber, a vegetable fiber, a wax, paraffin, starch, tragacanth, a cellulose derivative, polyethylene glycol, silicone, bentonite, silica, talc or zinc oxide.

When the formulation is a powder or a spray, carrier ingredients that may be used include lactose, talc, silica, aluminum hydroxide, calcium silicate or polyamide powder. Particularly, in the case of a spray, it may further include a propellent, such as chlorofluorohydrocarbon, propane/butane or dimethyl ether.

When the formulation is a solution or an emulsion, carrier ingredients that may be used include a solvent, a solvating agent or an emulsifying agent, such as water, ethanol, isopropanol, ethyl carbonate, ethyl acetate, benzyl alcohol, benzyl benzoate, propylene glycol, 1,3-butylglycol oil, glycerol fatty acid ester, polyethylene glycol or sorbitan fatty acid ester.

When the formulation is a suspension, carrier ingredients that may be used include a liquid diluent, such as water, ethanol or propylene glycol, a suspending agent, such as ethoxylated isostearyl alcohol, polyoxyethylene sorbitol ester or polyoxyethylene sorbitan ester, microcrystalline cellulose, aluminum metahydroxide, bentonite, agar, tragacanth, or the like.

When the formulation is a surfactant-containing cleanser, carrier ingredients that may be used include aliphatic alcohol sulfate, aliphatic alcohol ether sulfate, sulfosuccinic acid monoester, isethionate, imidazolinium derivative, methyl taurate, sarcosinate, fatty acid amide ether sulfate, alkylamidobetaine, aliphatic alcohol, fatty acid glyceride, fatty acid diethanolamine, vegetable oil, lanoline derivative, ethoxylated glycerol fatty acid ester, or the like.

The cosmetic composition according to an embodiment of the present disclosure may further include functional additives and other ingredients used currently in a cosmetic composition, besides the active ingredient. The functional additive may include an ingredient selected from the group consisting of a water-soluble vitamin, an oil-soluble vitamin, a polypeptide, a polypolysaccharide, a spingolipid and a seaweed extract.

In addition to the above-mentioned functional additives, the cosmetic composition according to an embodiment of the present disclosure may further include ingredients used conventionally in a cosmetic composition, if necessary, in combination with the functional additives. Such ingredients include an oil and fat ingredient, a moisturizing agent, an emollient, a surfactant, an organic and inorganic pigment, an organic powder, an UV absorbing agent, a preservative, a sterilizing agent, an antioxidant, a plant extract, a pH modifier, an alcohol, a colorant, a fragrance, a blood flow-stimulating agent, a coolant, an anti-perspirant, a purified water, or the like.

In addition, the skin whitening composition according to an embodiment of the present disclosure may be a preparation for external use on skin. The preparation for external use on skin generally refers to any preparation applied from the outside of the skin and may include various cosmetic and pharmaceutical formulations.

In still another aspect of the present disclosure, there is provided a skin whitening method which includes administering an effective amount of an adamantanecarboxylic acid benzyl amide derivative compound represented by Chemical Formula 1, an isomer thereof, a pharmaceutically acceptable salt thereof, a hydrate thereof or a solvate thereof, to a subject in need thereof.

In still another aspect of the present disclosure, there is provided use of an adamantanecarboxylic acid benzyl amide derivative compound represented by Chemical Formula 1, an isomer thereof, a pharmaceutically acceptable salt thereof, a hydrate thereof or a solvate thereof for skin whitening.

In still another aspect of the present disclosure, there is provided an adamantanecarboxylic acid benzyl amide derivative compound represented by Chemical Formula 1, an isomer thereof, a pharmaceutically acceptable salt thereof, a hydrate thereof or a solvate thereof, for use in skin whitening.

In yet another aspect of the present disclosure, there is provided use of an adamantanecarboxylic acid benzyl amide derivative compound represented by Chemical Formula 1, an isomer thereof, a pharmaceutically acceptable salt thereof, a hydrate thereof or a solvate thereof for the preparation of a skin whitening composition.

Modes for Invention

Hereinafter, the present disclosure will be explained in more detail with reference to examples. However, the following examples are for illustrative purposes only. In addition, it will be apparent to those skilled in the art that the scope of the present disclosure is not limited to the following examples.

EXAMPLES

Examples: Preparation of Novel Adamantanecarboxylic Acid Benzyl Amide Derivative Compound

[Example 1] Preparation of Adamantane-1-Carboxylic Acid 2,4-Dihydroxybenzylamide

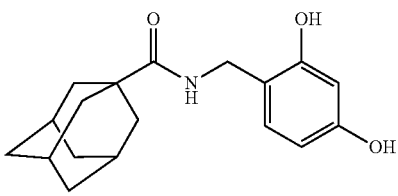 [SMILES: O=C(NCc1ccc(O)cc1O)C12CC3CC(CC(C3)C1)C2]

Adamantane-1-carboxylic acid (1.8 g) was dissolved in dichloromethane (50 mL), and then N-(3-dimethylaminopropyl)-N'-ethylcarbodiimide hydrochloride (EDC, 2.1 g), triethylamine (1.6 mL) and 2,4-dihydroxybenzyl amine (1.4 g) were added sequentially dropwise thereto. Then, the resultant mixture was agitated at room temperature for 5 hours. After completing the reaction, the reaction solution was washed with water and saturated sodium chloride, and the organic layer was dried with dry magnesium sulfate. The organic layer was filtered, concentrated under reduced pressure, and then separated by using chromatography to obtain the target compound, adamantane-1-carboxylic Acid 2,4-dihydroxybenzylamide (1.0 g).

$^1$H NMR (300 MHz, DMSO-$d_6$) δ 9.56 (brs, 1H), 9.11 (brs, 1H), 7.88 (brs, 1H), 6.79 (d, J=7.8 Hz, 1H), 6.21 (s, 1H), 6.15 (d, J=7.8 Hz, 1H), 4.05 (d, J=5.7 Hz, 2H), 1.96-1.65 (m, 15H).

[Example 2] Preparation of Adamantane-1-Carboxylic Acid 3,4-Dihydroxybenzylamide

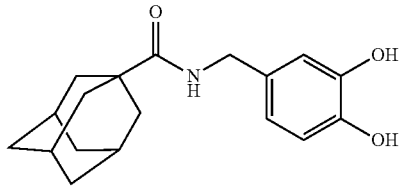 [SMILES: O=C(NCc1ccc(O)c(O)c1)C12CC3CC(CC(C3)C1)C2]

The target compound (1.6 g) was obtained in a solid state by using substantially the same method as Example 1, except that 3,4-dihydroxybenzylamine was used instead of 2,4-dihydroxybenzylamine.

$^1$H NMR (300 MHz, DMSO-$d_6$) δ 8.71 (brs, 2H), 7.77 (brs, 1H), 6.63-6.59 (m, 2H), 6.44 (d, J=7.8 Hz, 1H), 4.07 (d, J=5.7 Hz, 2H), 1.96-1.65 (m, 15H).

[Example 3] Preparation of Adamantane-1-Carboxylic Acid 3,5-Dihydroxybenzylamide

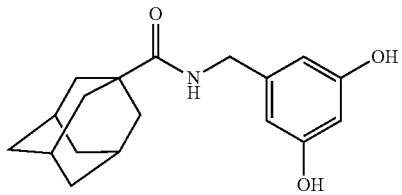 [SMILES: O=C(NCc1cc(O)cc(O)c1)C12CC3CC(CC(C3)C1)C2]

The target compound (0.9 g) was obtained in a solid state by using substantially the same method as Example 1, except that 3,5-dihydroxybenzylamine was used instead of 2,4-dihydroxybenzylamine.

$^1$H NMR (300 MHz, DMSO-$d_6$) δ 9.07 (brs, 2H), 7.79 (brs, 1H), 6.04-6.02 (m, 3H), 4.06 (d, J=5.7 Hz, 2H), 1.97-1.67 (m, 15H).

[Example 4] Preparation of Adamantane-1-Carboxylic Acid 2,5-Dihydroxybenzylamide

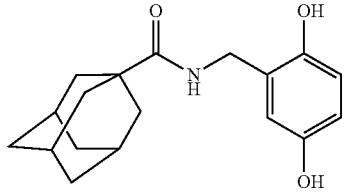 [SMILES: O=C(NCc1cc(O)ccc1O)C12CC3CC(CC(C3)C1)C2]

The target compound (1.2 g) was obtained in a solid state by using substantially the same method as Example 1, except that 2,5-dihydroxybenzylamine was used instead of 2,4-dihydroxybenzylamine.

$^1$H NMR (300 MHz, DMSO-$d_6$) δ 8.84 (brs, 1H), 8.59 (brs, 1H), 7.86 (brs, 1H), 6.56-6.42 (m, 3H), 4.09 (d, J=6.0 Hz, 2H), 1.98-1.67 (m, 15H).

[Example 5] Preparation of Adamantane-1-Carboxylic Acid 4-Hydroxybenzylamide

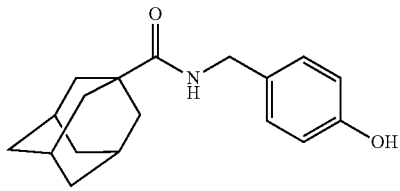 [SMILES: O=C(NCc1ccc(O)cc1)C12CC3CC(CC(C3)C1)C2]

The target compound (1.7 g) was obtained in a solid state by using substantially the same method as Example 1, except that 4-hydroxybenzylamine was used instead of 2,4-dihydroxybenzylamine.

$^1$H NMR (300 MHz, DMSO-$d_6$) δ 9.18 (brs, 1H), 7.80 (brs, 1H), 6.98 (d, J=7.8 Hz, 2H), 6.66 (d, J=7.8 Hz, 2H), 4.12 (d, J=6.0 Hz, 2H), 1.95-1.65 (m, 15H).

[Example 6] Preparation of Adamantane-1-Carboxylic Acid 3-Hydroxybenzylamide

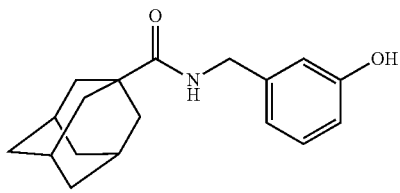 [SMILES: O=C(NCc1cccc(O)c1)C12CC3CC(CC(C3)C1)C2]

The target compound (1.5 g) was obtained in a solid state by using substantially the same method as Example 1, except that 3-hydroxybenzylamine was used instead of 2,4-dihydroxybenzylamine.

$^1$H NMR (300 MHz, DMSO-$d_6$) δ 9.26 (brs, 1H), 7.88 (brs, 1H), 7.09-7.03 (m, 1H), 6.61-6.56 (m, 3H), 4.16 (d, J=5.7 Hz, 2H), 1.97-1.67 (m, 15H).

[Example 7] Preparation of Adamantane-1-Carboxylic Acid 2-Hydroxybenzylamide

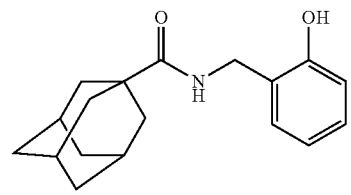 [SMILES: O=C(NCc1ccccc1O)C12CC3CC(CC(C3)C1)C2]

The target compound (1.5 g) was obtained in a solid state by using substantially the same method as Example 1, except that 2-hydroxybenzylamine was used instead of 2,4-dihydroxybenzylamine.

$^1$H NMR (300 MHz, DMSO-$d_6$) δ 9.58 (brs, 1H), 7.91 (brs, 1H), 7.04-6.98 (m, 2H), 6.77-6.71 (m, 2H), 4.17 (d, J=5.7 Hz, 2H), 1.97-1.66 (m, 15H).

Test Example: Effect of Inhibiting Melanin Formation in Melanocytes

Each of the amide derivative compounds according to Examples was determined in terms of the effect of inhibiting melanin formation in melanocytes by using the Dooley method. As a cell line, a mice-derived B16F10 (malignant melanoma cells) available from Korean Cell Line Bank was used. In addition, DMEM (Cat No. 11195), FBS (Cat No. 16000-044) and antibiotic-antifungal agent (Cat No. 15240-062) required for culturing cells were purchased from Invitrogen (GIBCO).

The cell line was cultured at 37° C. under 5% $CO_2$. The cultured B16F10 cells were stripped off with 0.05% trypsin-EDTA, the same number of cells ($1\times10^4$ cells/well) was inoculated into a 48-well plate, and then the medium was exchanged with a medium containing 10 ppm of each Example continuously for 3 days from the next day. As a positive control, kojic acid and 5-adamantan-1-yl-N-(2,4-dihydroxybenzyl)-2,4-dimethoxybenzamide were used.

After the fifth day, the cells were treated with 1 N NaOH to carry out reaction at 60° C. for 2 hours so that melanin contained in the cells might be dissolved, and then the amount of melanin was measured by determining the absorbance at 405 nm. Then, the concentration ($IC_{50}$) of each Example required for reducing melanin formation by half in melanocytes was calculated. The results are shown in the following Table 1.

TABLE 1

| Compound | Inhibition of melanin formation $IC_{50}$ (μM) |
|---|---|
| Kojic acid | 500 |
| 5-adamantan-1-yl-N-(2,4-dihydroxybenzyl)-2,4-dimethoxybenzamide | 1.1 |
| Example 1 | 15.05 |
| Example 2 | 0.02 |
| Example 3 | 20.57 |
| Example 4 | 1.43 |
| Example 5 | 11.11 |
| Example 6 | 0.48 |
| Example 7 | 2.36 |

Referring to the above results, in the case of the positive control, kojic acid, a concentration of 500 μM is required for inhibiting melanin formation. As compared to this, each of Examples 1-7 can inhibit melanin formation even at a concentration of 0.02-15.05 μM. Particularly, in the case of 5-adamantan-1-yl-N-(2,4-dihydroxybenzyl)-2,4-dimethoxybenzamide used as a positive control, a concentration of 1.1 μM is required for inhibiting melanin formation. On the contrary, in the case of Examples 2 and 6, they can inhibit melanin formation even at a concentration of 0.02 μM and 0.48 μM, respectively, suggesting that they have an excellent whitening effect.

Hereinafter, some formulation examples of the skin whitening composition according to an embodiment of the present disclosure will be explained, but the skin whitening composition according to an embodiment of the present disclosure may be applied to other various formulations. Therefore, the following examples are for illustrative purposes only, and the scope of the present disclosure is not limited thereto.

[Formulation Example 1] Skin Toner

A skin toner was prepared according to the composition as shown in the following Table 2 by the conventional method.

TABLE 2

| Ingredients | Content (wt %) |
| --- | --- |
| Example | 0.1 |
| Glycerin | 3.0 |
| Butylene glycol | 2.0 |
| Propylene glycol | 2.0 |
| Carboxyvinyl polymer | 0.1 |
| PEG 12 nonyl phenyl ether | 0.2 |
| Polysorbate 80 | 0.4 |
| Ethanol | 10.0 |
| Triethanolamine | 0.1 |
| Preservative, Pigment, Fragrance | Q.S. |
| Purified water | Balance |

[Formulation Example 2] Nutrient Cream

A nutrient cream was prepared according to the composition as shown in the following Table 3 by the conventional method.

TABLE 3

| Ingredients | Content (wt %) |
| --- | --- |
| Example | 2.0 |
| Polysorbate 60 | 1.5 |
| Sorbitan sesquioleate | 0.5 |
| PEG 60 cured castor oil | 2.0 |
| Liquid paraffin | 10.0 |
| Squalane | 5.0 |
| Caprylic/capric triglyceride | 5.0 |
| Glycerin | 5.0 |
| Butylene glycol | 3.0 |
| Propylene glycol | 3.0 |
| Triethanolamine | 0.2 |
| Preservative, Pigment, Fragrance | Q.S. |
| Purified water | Balance |

[Formulation Example 3] Massage Cream

A massage cream was prepared according to the composition as shown in the following Table 4 by the conventional method.

TABLE 4

| Ingredients | Content (wt %) |
| --- | --- |
| Example | 1.0 |
| Beeswax | 10.0 |
| Polysorbate 60 | 1.5 |
| PEG 60 cured castor oil | 2.0 |
| Sorbitan sesquioleate | 0.8 |
| Liquid paraffin | 40.0 |
| Squalane | 5.0 |
| Caprylic/capric triglyceride | 4.0 |
| Glycerin | 5.0 |
| Butylene glycol | 3.0 |
| Propylene glycol | 3.0 |
| Triethanolamine | 0.2 |
| Preservative, Pigment, Fragrance | Q.S. |
| Purified water | Balance |

[Formulation Example 4] Pack

A pack was prepared according to the composition as shown in the following Table 5 by the conventional method.

TABLE 5

| Ingredients | Content (wt %) |
| --- | --- |
| Example | 0.2 |
| Polyvinyl alcohol | 13.0 |
| Sodium carboxymethyl cellulose | 0.2 |
| Glycerin | 5.0 |
| Allantoin | 0.1 |
| Ethanol | 6.0 |
| PEG 12 nonyl phenyl ether | 0.3 |
| Polysorbate 60 | 0.3 |
| Preservative, Pigment, Fragrance | Q.S. |
| Purified water | Balance |

[Formulation Example 5] Gel

A gel was prepared according to the composition as shown in the following Table 6 by the conventional method.

TABLE 6

| Ingredients | Content (wt %) |
| --- | --- |
| Example | 0.5 |
| Sodium ethylenediamine acetate | 0.05 |
| Glycerin | 5.0 |
| Carboxyvinyl polymer | 0.3 |
| Ethanol | 5.0 |
| PEG 60 cured castor oil | 0.5 |
| Triethanol amine | 0.3 |
| Preservative, Pigment, Fragrance | Q.S. |
| Purified water | Balance |

[Formulation Example 6] Ointment

An ointment was prepared according to the composition as shown in the following Table 7 by the conventional method.

TABLE 7

| Ingredients | Content (wt %) |
| --- | --- |
| Example | 1.5 |
| Glycerin | 8.0 |
| Butylene glycol | 4.0 |
| Liquid paraffin | 15.0 |
| Beta-glucan | 7.0 |
| Carbomer | 0.1 |
| Caprylic/capric triglyceride | 3.0 |
| Squalane | 1.0 |
| Cetearyl glucoside | 1.5 |
| Sorbitan stearate | 0.4 |
| Cetearyl alcohol | 1.0 |
| Beeswax | 4.0 |
| Preservative, Pigment, Fragrance | Q.S. |
| Purified water | Balance |

The invention claimed is:

1. A skin whitening method comprising administering an effective amount of the adamantanecarboxylic acid benzyl amide derivative compound represented by Chemical Formula 1-5, Chemical Formula 1-6, or Chemical Formula 1-7, an isomer thereof, a pharmaceutically acceptable salt thereof, a hydrate thereof or a solvate thereof, to a subject in need thereof:

[Chemical Formula 1-5]

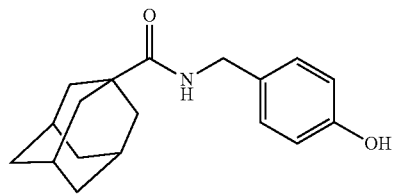

[Chemical Formula 1-6]

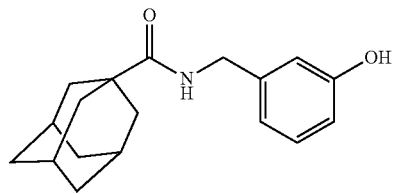

[Chemical Formula 1-7]

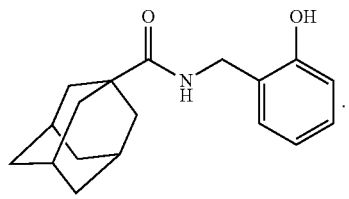

2. The skin whitening method according to claim 1, wherein the compound, isomer thereof, pharmaceutically acceptable salt thereof, prodrug thereof, hydrate thereof or solvate thereof is formulated in a form of a composition, wherein the composition comprises the compound, isomer thereof, pharmaceutically acceptable salt thereof, prodrug thereof, hydrate thereof or solvate thereof in an amount of 0.01-20 wt % based on the total weight of the composition.

3. The skin whitening method according to claim 1, wherein the compound, isomer thereof, pharmaceutically acceptable salt thereof, prodrug thereof, hydrate thereof or solvate thereof inhibits melanin formation.

4. The skin whitening method according to claim 2, wherein the composition is a pharmaceutical composition.

5. The skin whitening method according to claim 2, wherein the composition is a cosmetic composition.

6. The skin whitening method according to claim 2, wherein the composition is a preparation for external use on skin.

7. The skin whitening method according to claim 1, wherein the adamantanecarboxylic acid benzyl amide derivative compound is a compound represented by Chemical Formula 1-5:

[Chemical Formula 1-5]

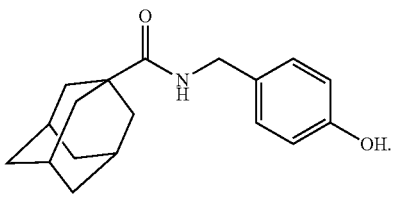

8. The skin whitening method according to claim 1, wherein the adamantanecarboxylic acid benzyl amide derivative compound is a compound represented by Chemical Formula 1-6:

[Chemical Formula 1-6]

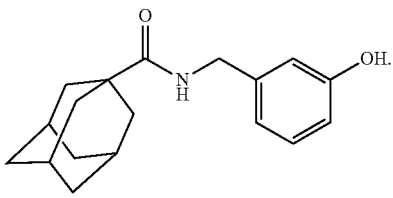

9. The skin whitening method according to claim 1, wherein the adamantanecarboxylic acid benzyl amide derivative compound is a compound represented by Chemical Formula 1-7:

[Chemical Formula 1-7]

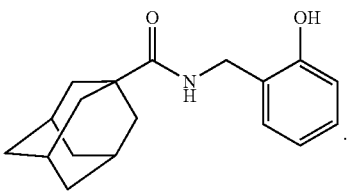

* * * * *